United States Patent [19]

Schaar

[11] 3,978,861
[45] Sept. 7, 1976

[54] DISPOSABLE DIAPER WITH END FLAP MEANS AND METHOD

[75] Inventor: Charles H. Schaar, Lake Zurich, Ill.

[73] Assignee: Colgate-Palmolive Company, New York, N.Y.

[22] Filed: Sept. 15, 1975

[21] Appl. No.: 613,603

Related U.S. Application Data

[62] Division of Ser. No. 472,531, May 23, 1974, Pat. No. 3,930,501.

[52] U.S. Cl. ............................... 128/287; 128/284
[51] Int. Cl.² ........................................ A61F 13/16
[58] Field of Search ............................ 128/287, 284

[56] References Cited
UNITED STATES PATENTS

| | | |
|---|---|---|
| 3,386,442 | 6/1968 | Sabee ................................. 128/287 |
| 3,402,715 | 9/1968 | Liloia et al. ........................ 128/287 |
| 3,721,242 | 3/1973 | Krusko ............................... 128/287 |
| 3,794,038 | 2/1974 | Buell ................................. 128/287 |

Primary Examiner—Aldrich F. Medberry
Attorney, Agent, or Firm—Powell L. Sprunger

[57] ABSTRACT

A disposable diaper having an absorbent pad, a fluid impervious backing sheet defining a back surface of the diaper, a front surface, and a plurality of longitudinally extending folds defining a box-pleat configuration of the diaper. An end flap of the box-pleat diaper is folded over the front surface of the diaper, and means is provided for retaining a least a portion of the front surface of the flap against the underlying front surface of the box-pleat diaper.

2 Claims, 25 Drawing Figures

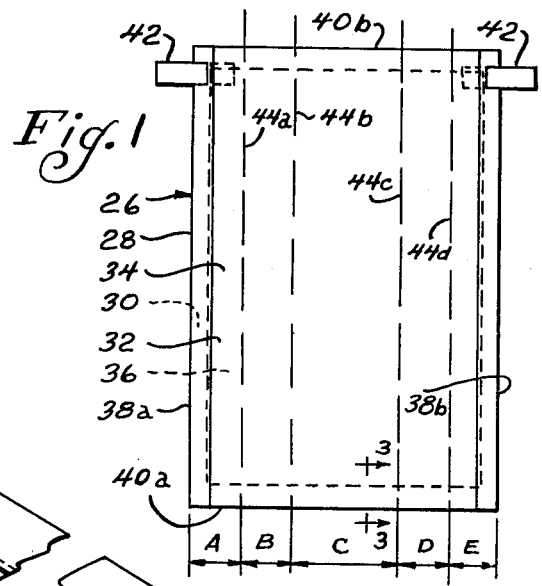
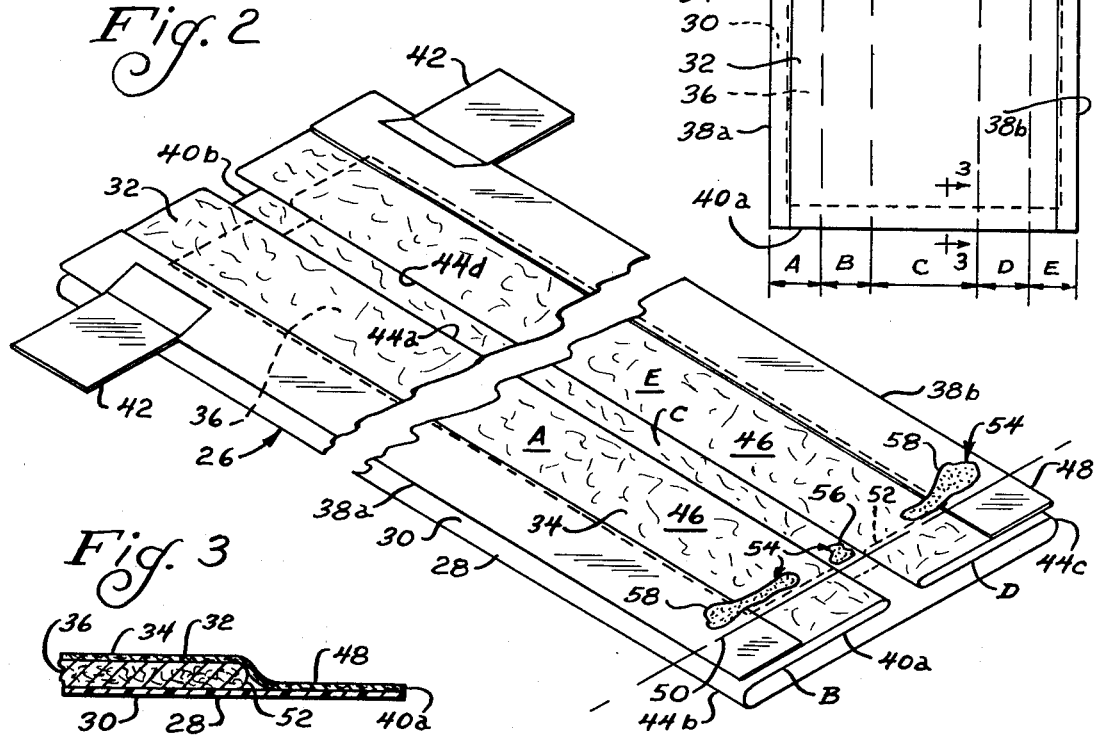
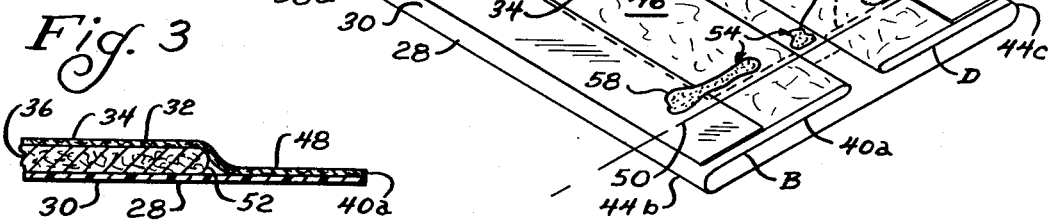
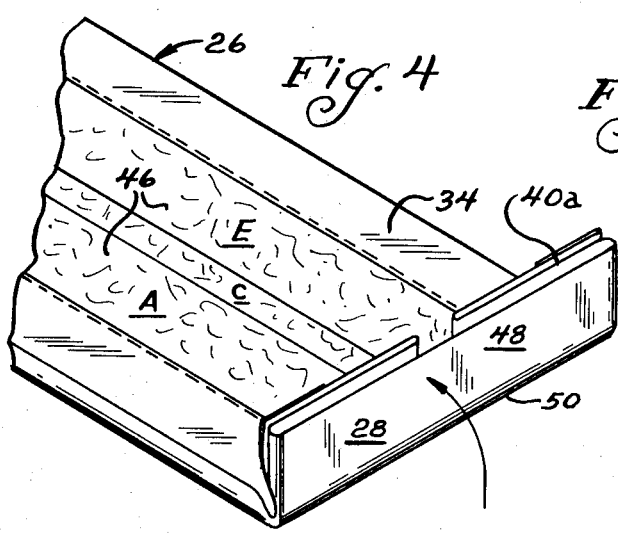
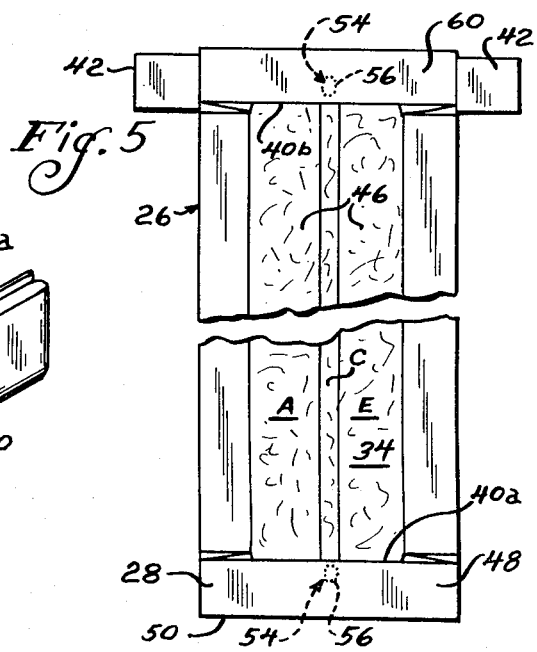

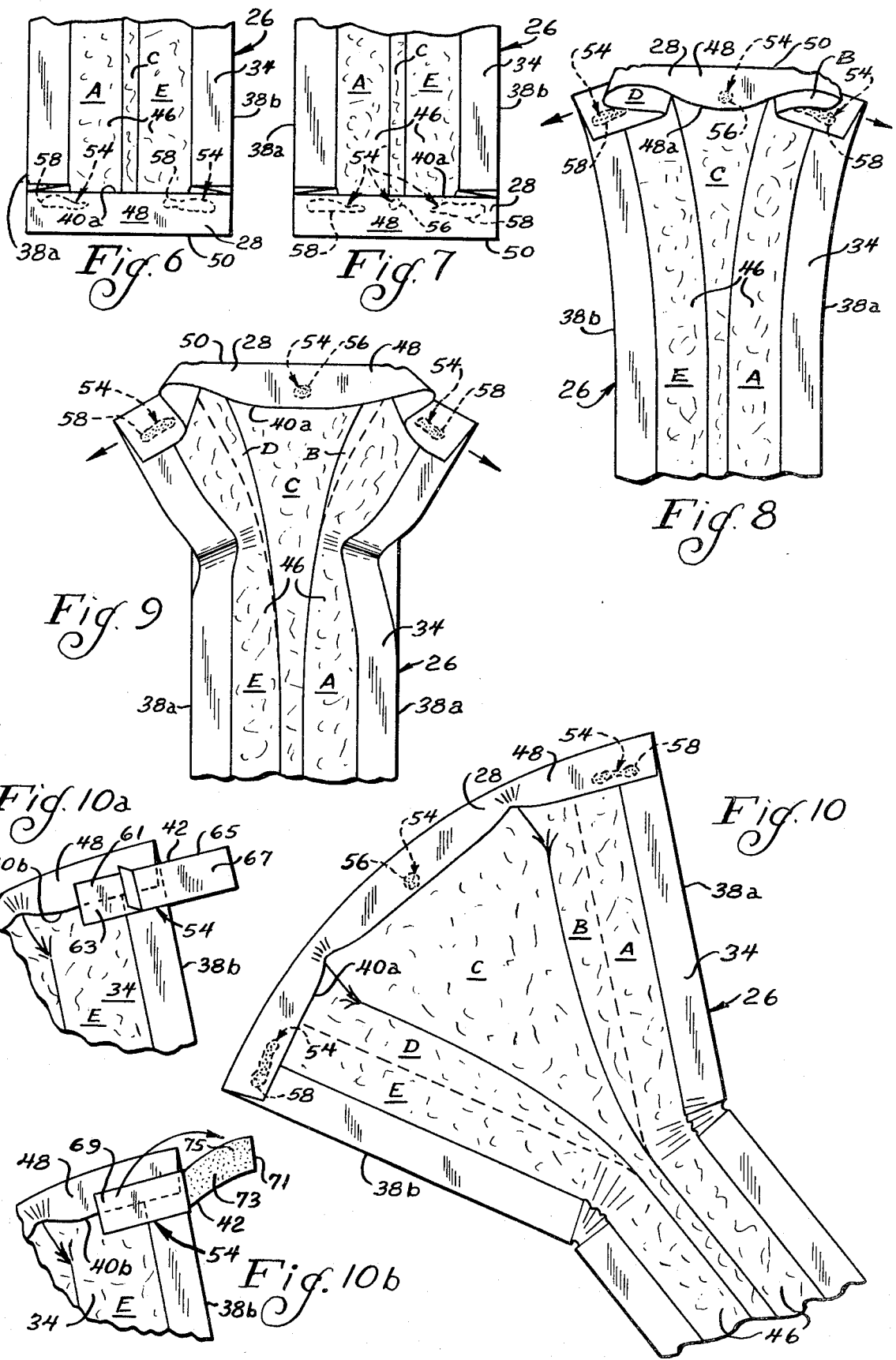

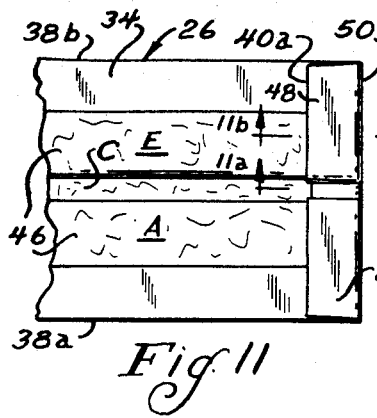
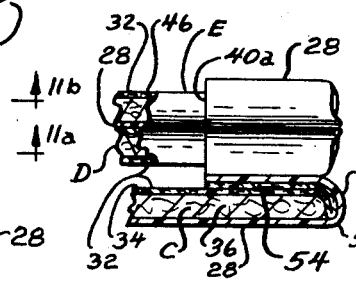
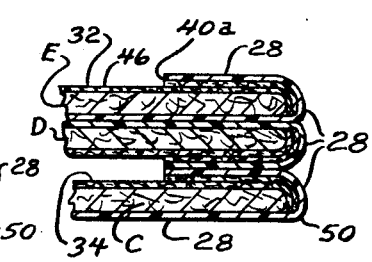
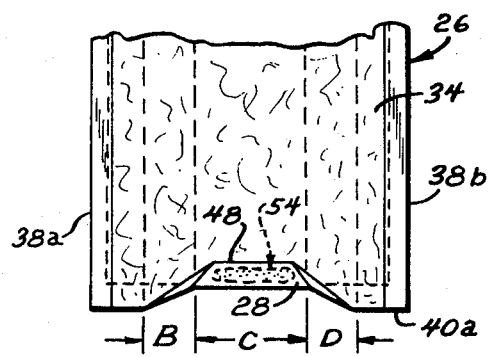
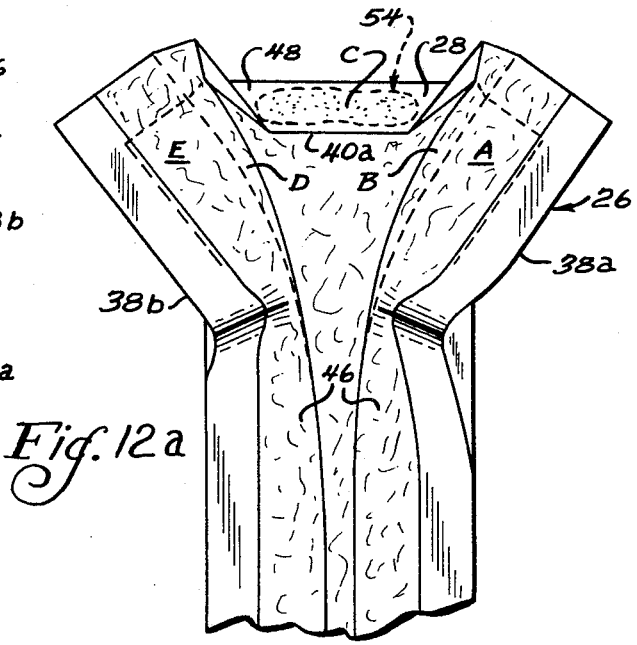
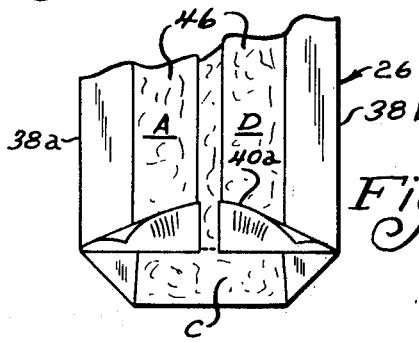
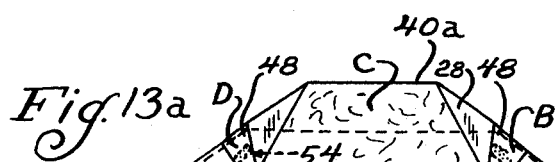
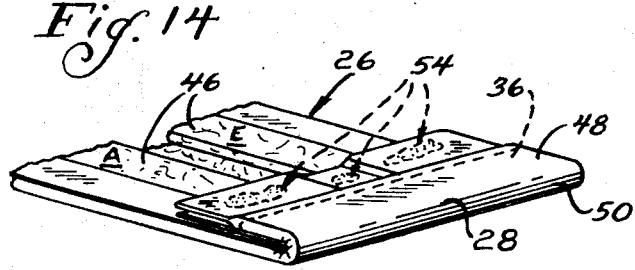
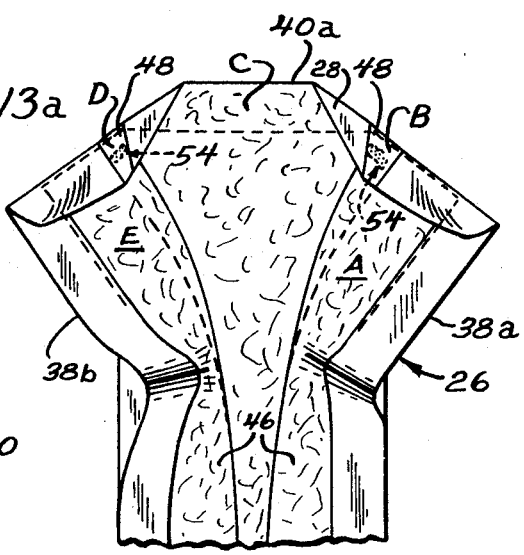

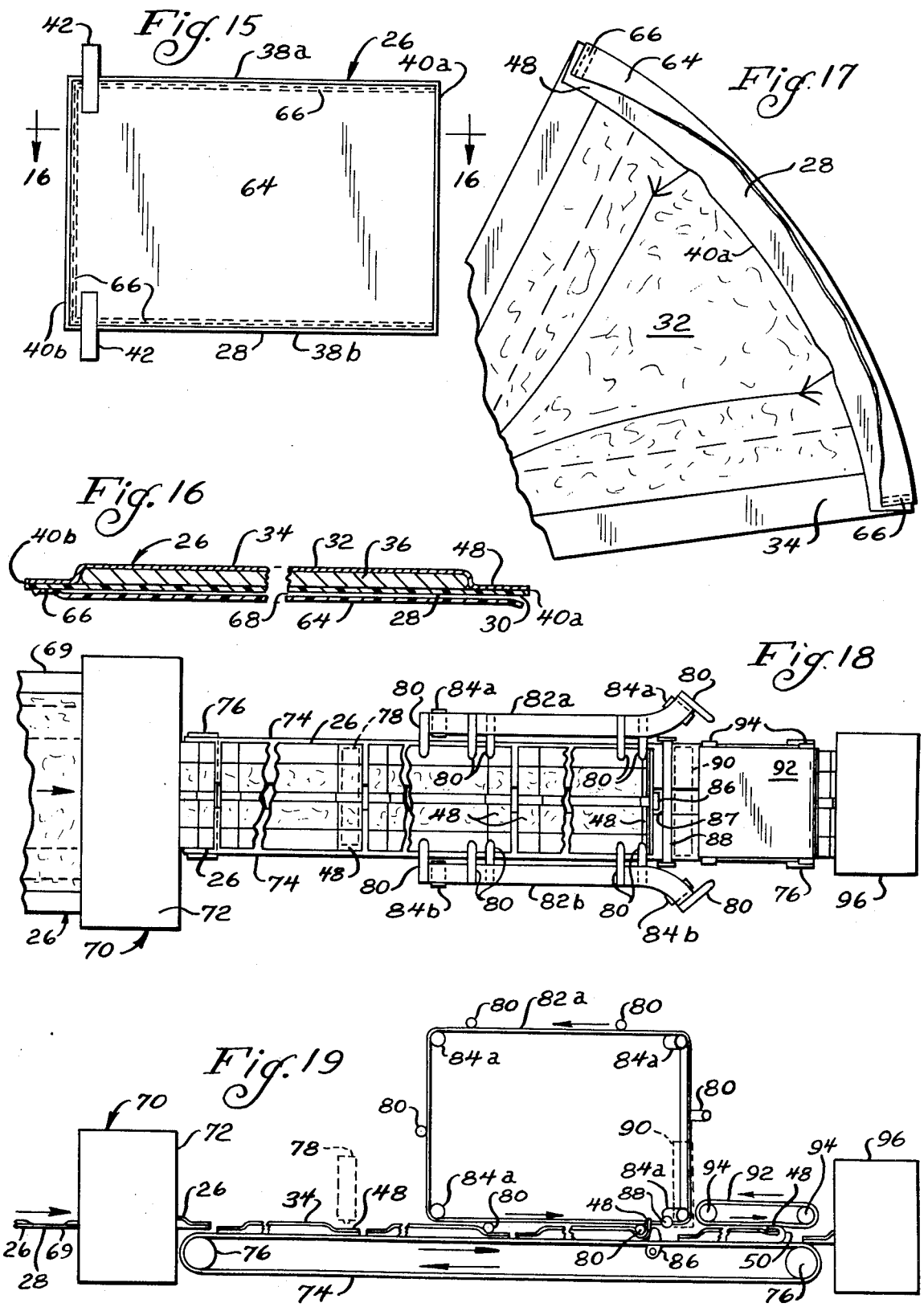

3,978,861

DISPOSABLE DIAPER WITH END FLAP MEANS AND METHOD

This is a division, of application Ser. No. 472,531 filed May 23, 1974, now U.S. Pat. No. 3,930,501.

BACKGROUND OF THE INVENTION

The present invention relates to disposable diapers for infants, and more particularly to diapers which prevent leakage.

During recent years diapers of the disposable type have come into widespread use. Such diapers are generally constructed having a fluid impervious backing sheet, a fluid pervious top sheet, and an absorbent pad located between the top and backing sheets. Although disposable diapers have attained a high degree of popularity with parents due to convenience, many unfavorable comments have been made about recurrent leakage of the diapers during use. In particular, the ends of the diapers are normally susceptible to leakage due to wicking of urine from the ends of the absorbent pad or a loose fit of the diaper about the infant.

This problem of leakage at the ends of the diaper is compounded by the structure of the diaper itself. Many of the present disposable diapers have tape strips located adjacent one end of the diapers. The diapers are normally placed on the infant by laying the infant on the diaper with the strip bearing part of the diaper being located beneath the back waistline of the infant. After removal of the tape strips from release sheets, attachment portions of the strips are brought around the infant's legs, and anchored to the front portion of the diaper. However, in order to obtain a tight fit of the diaper and prevent leakage about the infant's legs, the attachment portions of the strips are frequently secured at a location on the front portion of the diaper which is spaced somewhat from the front end edge or waistline of the diaper.

Since the permanently anchored portions of the strips are located adjacent the back end edge of the diaper, after placement of the diaper these strip portions apply tension to the back waistline of the diaper and thus maintain a close fit of the diaper against the back waistline of the infant. In contrast, the attachment portions of the strips are often spaced from the front waistline of the diaper, and significant tension is not applied by the strips against the diaper front waistline. The front waistline of the diaper is thus permitted to gap away from the infant, increasing the possibility of urine leakage in this area of the diaper. However, the front waistline of the diaper is normally more susceptible to urine leakage than the back waistline, since it is closer to the site of urine deposition on the diaper. Also, infants are generally inclined to spend more time lying on their stomachs than their backs, causing gravity to drive urine in the diaper with greater frequency toward the front waistline. Thus, the diaper ends are normally susceptible to leakage where it should most be prevented.

SUMMARY OF THE INVENTION

A principle feature of the present invention is the provision of a disposable diaper of simplified construction which prevents leakage at an end edge of the diaper.

The diaper of the present invention has an absorbent pad, a fluid impervious backing sheet, a pair of side edges, a pair of end edges connecting the side edges, with the backing sheet extending to at least one end edge of the diaper, and a front surface. The diaper includes a box-pleat fold which defines a longitudinally extending central panel, a pair of first pleat panels extending from and overlying the central panel, and a pair of second pleat panels extending from and overlying the first pleat panels. The diaper has flap means adjacent the one end edge of the diaper which has its front surface folded against the front surface of an inner adjacent portion of the diaper relative the one end edge. Means is provided for securing the front surface of the flap means to the front surface of the adjacent portion of the diaper.

A feature of the invention is that when the end of the box-pleat diaper adjacent the flap means is unfolded for placement of the diaper on an infant, the securing means retains the front surface of the flap means against the front surface of the adjacent portion of the diaper.

Another feature of the invention is that the flap means includes a portion of the fluid impervious backing sheet, and the folded over flap means prevents leakage from the diaper end during use.

A further feature of the invention is that the folded over flap means may cover an end of the absorbent pad and prevent leakage due to wicking from the pad during use.

Still another feature of the invention is that the securing means in the unfolded diaper may be spaced apart to permit the flap means to engage against and form a gasket with the infant's skin to prevent leakage.

Another feature of the invention is the provision of a method for making disposable diapers of the invention in a simplified manner.

Further features will become more fully apparent in the following description of the embodiments of this invention and from the appended claims.

DESCRIPTION OF THE DRAWINGS

In the drawings:

FIG. 1 is a plan view of a flat disposable diaper;

FIG. 2 is a fragmentary perspective view of the diaper of FIG. 1 after having been folded into a box-pleat configuration;

FIG. 3 is a sectional view taken substantially as indicated along the line 3—3 of FIG. 1;

FIG. 4 is a fragmentary perspective view illustrating the formation of a diaper of the present invention;

FIG. 5 is a fragmentary plan view of a diaper of the present invention;

FIG. 6 is a fragmentary plan view of another embodiment of the diaper of the present invention;

FIG. 7 is a fragmentary plan view of another embodiment of the diaper of the present invention;

FIGS. 8–10b are fragmentary plan views illustrating configurations of the diapers of FIG. 7 as the diaper is unfolded for placement on an infant;

FIG. 11 is a fragmentary plan view of another embodiment of the diaper of the present invention;

FIG. 11a is a fragmentary sectional view taken substantially as indicated along the line 11a—11a of FIG. 11;

FIG. 11b is a fragmentary sectional view taken substantially as indicated along the line 11b—11b of FIG. 11;

FIGS. 12 and 12a are fragmentary plan views illustrating another embodiment of the diaper of the present invention;

FIGS. 13 and 13a are fragmentary plan views of another embodiment of the diaper of the present invention;

FIG. 14 is a fragmentary perspective view of another embodiment of the diaper of the present invention;

FIG. 15 is a plan view of the back side of another embodiment of the diaper of the present invention;

FIG. 16 is a fragmentary sectional view taken substantially as indicated along the line 16—16 of FIG. 15;

FIG. 17 is a fragmentary perspective view of the partially unfolded diaper of FIG. 15 during placement;

FIG. 18 is a top diagrammatic view of a device for making diapers according to a method of the present invention; and FIG. 19 is an elevational diagrammatic view of the device of FIG. 18.

DESCRIPTION OF THE PREFERRED EMBODIMENTS

Referring now to FIGS. 1 and 3, there is shown a flat diaper designated generally 26 having a fluid impervious backing sheet 28 defining a back surface 30 of the diaper, a fluid pervious top sheet 32 defining a substantial portion of a front surface 34 of the diaper, and an absorbent pad 36 positioned intermediate the backing sheet 28 and cover sheet 32. The diaper 26 has a pair of side edges 38a and 38b, and a pair of end edges 40a and 40b connecting the side edges 38a and b. The diaper 26 may also have a pair of conventional tape fasteners 42 adjacent one end edge 40b of the diaper for securing the diaper about an infant during placement. As best shown in FIG. 3, the top and backing sheets 32 and 28, respectively, may extend to the end edges of the diaper.

The flat diaper 26 of FIG. 1 has a plurality of longitudinally extending folds about fold lines 44a, 44b, 44c, and 44d, defining a box-pleat configuration of the diaper, as shown in FIG. 2. As illustrated in FIGS. 1 and 2, the box-pleat diaper 26 has a longitudinally extending central panel C, a pair of first pleat panels B and D extending from and overlying the central panel C, and a pair of second pleat panels or outermost pleat sections A and E extending from and overlying the first pleat panels B and D. The pleats 46 of the box-pleat diaper may be spaced apart in a lateral central portion of the diaper, as shown in FIG. 2, for a purpose which will be described below.

As illustrated in FIGS. 2–4, the box-pleat diaper 26 has an end section or flap 48 adjacent the end edge 40a, which is folded about a lateral fold line 50 over the front surface 34 of the diaper, such that the front surface 34 of the end section or flap means 48 engages against the front surface 34 of the diaper adjacent the end section 48. Preferably, the end edge 52 of the absorbent pad 36 most adjacent the end edge 40a of the diaper is spaced from the end edge 40a, and the fold line 50 of the end section 48 is located adjacent the end edge 52 of the absorbent pad 36, in order that the backing sheet 28 in the end section 48 overlies an end portion of the absorbent pad when the end section is folded into place on top of the diaper.

As illustrated in FIG. 2, the diaper 26 has securing or retaining means generally designated 54, such as adhesive, adjacent the fold line 50 to retain at least a portion of the front surface 34 of the end section 48 against the underlying front surface 34 of the box-pleat diaper. Although for convenience the securing means 54 is described in connection with the use of adhesive, it will be understood that other suitable securing means may be utilized to retain the front surface of the end section to the underlying front surface of the diaper, such as by heat sealing or tape strips. It is also understood that the adhesive may be totally or partially deposited upon the end section 48 itself, if desired. After the end section 48 has been folded over the top of the diaper, the end section 48 may be pressed against the underlying portion of the diaper to obtain a good set of the adhesive and retain the end section 48 in place.

In the embodiment of the diaper 26 illustrated in FIGS. 2 and 7, the securing means 54 comprises a spot of adhesive 56 intermediate the pleats 46 on the front surface 34 of the central panel C adjacent the fold line 50, and a pair of adhesive lines 58 on the front surface of the second pleat panels A and E adjacent the fold line 50. The adhesive spot 56 retains the front surface 34 of the central panel C in the end section 48 against the underlying front surface 34 of the central panel C of the diaper. Similarly, the adhesive lines 58 retain the front surface 34 of the second pleat panels A and E in the end section 48 against the front surface 34 of the underlying portions of the second pleat panels in the diaper. In the embodiment of the diaper illustrated in FIG. 6, the securing means 54 comprises lines of adhesive 58 which retain the front surface of the second pleat panels A and E to the front surface 34 of the underlying second pleat panels. In the embodiment of the diaper illustrated in FIG. 5, the securing means 54 comprises the spot of adhesive 56 which retains the front surface 34 of the central panel C in the end section 48 to the underlying front surface 34 of the diaper central panel. The diaper of FIG. 5 also illustrates that the diaper may have a second end section 60 adjacent the other end of the diaper which is folded over the top of the diaper and retained in place by securing means 54, if desired. Preferably, the adhesive lines or spots 58 of the embodiments of the diaper shown in FIGS. 2 and 7 and FIG. 6 extend to adjacent the side edges 38a and b of the diaper.

The use of the folded over end section 48 to prevent leakage of urine from diaper is described in connection with the diaper embodiment of FIGS. 2 and 7, as illustrated in FIGS. 8–10. As the end of box-pleat diaper 26 adjacent the end section 48 is unfolded during placement of the diaper on an infant, the spots of adhesive 56 and 58 or securing means 54 maintain front surface portions of the end section 48 against the underlying front surface 34 of the diaper. Thus, as shown in FIGS. 8 and 9, as the second pleat panels A and E of the diaper are spread outwardly, the second pleat panels of the end section 48 are unfolded from under the central panel C of the end section. When the end of the diaper is completely unfolded, as shown in FIG. 10, the securing means 54 retains the entire length of the end section 48 in an overlying relationship with the portion of the diaper adjacent the end section 48. In this configuration of the diaper, the adhesive spot 56 retains the central panel C of the end section 48 against the underlying portion of the diaper central panel, while the adhesive lines 58 retain the second pleat panels of the end section 48 against the underlying second pleat panels of the diaper. It is apparent that the securing means 54 of the diapers of FIGS. 5 and 6 operate in the same manner to retain the end section 48 in an overlying relationship with the adjacent portion of the diaper when the box-pleat diaper is unfolded for placement.

Accordingly, when the box-pleat diaper is completely unfolded, the folded over portion of the fluid impervious backing sheet 28 serves to form a waterproof sealing barrier to prevent leakage at the end of the diaper. Moreover, since the folded over backing sheet in the end section preferably overlies an end portion of the absorbent pad, the backing sheet forms a waterproof pocket to capture urine which may wick from the end edge of the absorbent pad, and thus prevent leakage. It is also noted that the securing means 54 of the unfolded diaper of FIG. 10 retains only spaced areas of the end section against the diaper. Thus, the regions of the backing sheet in the end section 48 intermediate the adhesive spots 56 and 58 are permitted to gap away from the underlying front surface of the diaper and engage against the infant's skin. These free regions of the end section serve to form a gasket against the infant's skin and thus aid in preventing leakage of urine from the diaper.

Alternate embodiments of the securing means 54 are illustrated on an unfolded diaper in FIGS. 10a and 10b. In both embodiments, the tape fastener 42 itself secures the end section 48 against the underlying front surface 34 of the diaper. The tape fastener 42 of FIG. 10a comprises a tape strip 61 having an inner end portion 63 with adhesive on its underlying surface, which is utilized to secure the front surface of the second pleat panels in the end section 48 to the underlying front surface of the diaper. The tape strip 61 also includes an outer end portion 65 having adhesive on its upper surface which is covered by a release sheet 67. The release sheet 67 is removed from the outer end portion 65 of the tape strip 61 to expose the adhesive thereon for use in placement of the diaper on the infant.

The tape fastener of FIG. 10b comprises a release sheet 69 having adhesive on its underlying surface. The release sheet 69 retains the front surface of the second pleat panels in the end section 48 to the underlying front surface of the diaper. The fastener also comprises a tape strip 71 extending from the backside of the diaper and having adhesive 73 on one surface of an end section 75 which faces the release sheet 69. The end section 75 of the tape strip 71 is retained against the release sheet 69 by the adhesive 73 prior to use of the diaper, and is peeled from the release sheet for placement of the diaper on the infant. It is understood that the diapers of FIGS. 10a and b may have the spot of adhesive 56 described in connection with FIG. 7, or may omit such adhesive spot, as desired.

Another embodiment of the diaper is illustrated in FIGS. 11, 11a, and 11b, in which like reference numerals designate like parts. In this embodiment of the diapers, the front surfaces of the various panels in the end section 48 are folded directly against the front surfaces of the corresponding diaper panels adjacent the end section. To be more specific, the central panel C of the end section 48 has its front surface folded against the front surface of the central panel C adjacent the end section. The first pleat panels B and D of the end section 48 have their front surfaces folded against the front surfaces of the first pleat panels of the diaper adjacent the end section beneath the pleats 46. The second pleat panels A and E of the end section 48 have their front surfaces folded against the front surface of the second pleat panels of the diaper adjacent the end section 48 above the pleats 46. Thus, the central panel and first pleat panels of the end section are tucked under the pleats 46 of the diaper. It is apparent that the end section 48 may be readily folded in this manner by folding the end section over the flat diaper of FIG. 1 prior to folding the diaper into the box-pleat configuration of FIG. 2. It is apparent that the pleats of the box-pleat diaper retain the end section 48 in place. However, if desired, securing means 54, such as adhesive, may be utilized at selected positions laterally along the end section 48 to retain the end section in place on top of the diaper when the diaper is unfolded for use. The end section of this embodiment of the diaper serves to prevent urine leakage in the same manner as previously discussed in connection with the diapers of FIGS. 1–10.

Another embodiment of the diaper is illustrated in FIGS. 12 and 12a in which the central panel C of the end section 48 is tucked under the pleats 46 and is secured to the underlying portion of the central panel of the diaper by securing means 54, such as adhesive. A similar embodiment is shown in FIGS. 13 and 13a in which the first pleat panels B and D in the end section 48 are tucked under the pleats 46 and retained by adhering means 54, such as adhesive, to the respective first pleat panels of the diaper adjacent the end section 48. It is apparent that the diapers of FIGS. 12 and 13 operate in the same fashion as the diaper previously discussed to retain the end section 48 in place when the box-pleat diaper is unfolded for placement on an infant.

In FIG. 14 there is illustrated another embodiment of the diaper of the present Invention in which the end section 48 includes an end portion of the absorbent pad 36. The end section 48, which is folded over the top of the diaper, may be secured in place by securing means 54 in a manner as previously described in connection with the diapers of FIGS. 2–7. Since the end section 48 of the diaper of FIG. 14 includes an end portion of the absorbent pad, the end section 48 has more bulk and rigidity when the box-pleat diaper is unfolded for placement. The end section thus serves to reinforce this waistband portion of the diaper.

Another embodiment of the diaper of the present invention is illustrated in FIGS. 15–17, in which like reference numerals designate like parts. In this embodiment, the diaper 26 has a covering sheet 64 which overlies the back surface 30 of the backing sheet 28. The covering sheet 64 may be secured to the backing sheet 28 along a line 66 following the side edges 38a and b and end edge 40b by securing means, such as adhesive or heat sealing. Thus the covering sheet 64 and backing sheet 28 define a pocket 68 intermediate the sheets which is closed along the side edges 38a and b and end edge 40b, while it is open along at least a substantial portion of the end edge 40a. When the diaper 26 is folded into its box-pleat configuration, the end section 48 is folded over the top of the diaper, and the diaper is subsequently unfolded for placement on an infant, the end section 48 of the diaper serves to retain the pocket in a somewhat closed configuration, as illustrated in FIG. 17. After use of the diaper and removal from the infant, the parent may place his hand within the pocket 68 and grasp the diaper adjacent the end edge 40b of the diaper. The parent then may pull on this end of the diaper to invert the diaper and cover the front soiled surface 34 with the covering sheet 64 for disposal of the diaper.

A device 70 for folding diapers of the present invention is illustrated in FIGS. 18 and 19. In the device 70, a continuous sheet 69 of flat diapers 26 having a continuous fluid impervious backing sheet 28 is fed into an apparatus 72 which folds the sheet of flat diapers into a box-pleat configuration and cuts the diapers at their appropriate lengths. The diapers 26 are then fed from the apparatus 72 onto a pair of spaced endless conveyor belts 74 supported and driven by rollers 76. As the box-pleat diapers 26 move along the conveyor belts 74, i.e., to the right as viewed in FIGS. 18 and 19, in one embodiment of the device 70, means 78 deposits adhesive on a front surface 34 of the diapers adjacent end sections 48 of the diapers.

A pair of endless belts 82a and 82b are supported and driven by a plurality of rollers 84a and 84b, respectively, on opposite sides of the conveyor belts 74. A plurality of fingers 80 are secured to and extend inwardly from both of the belts 82a and b toward the belts 74. The upstream portions of the belts 82a and b are located adjacent side edges of the belts 74, and the lower courses of the belts 82a and b are located slightly above the belts 74, in order to bring the ends of the fingers 80 into position engaging the sides of the diapers adjacent the inner areas of the end sections 48 relative the longitudinal center of the diapers. The rollers 84a and b at the downstream portions of the belts 82a and b are spaced away at an incline from the belts 74 to remove the fingers 80 from the diapers for a purpose which will be described below.

The speed of travel of the belts 82a and b and the belts 74 is approximately the same, such that the fingers 80 move with and hold down the end sections 48 of the diapers as the diapers are conveyed along the belts 74. The diapers 26 travel along the belts 74 until they reach a cam 86 which moves upwardly through a spacing 87 between the belts 74, in order to deflect the end sections 48 away from the belts 74. The cam 86 is then withdrawn away from the upwardly deflected end sections of the diapers, while the end sections strike a rod 88 which extends laterally across the belts 74. As the diapers 26 pass under the rod 88, the end sections 48 are folded over the fingers 80 and the top of the diaper by the rod 88. If the means 78 has been utilized to deposit adhesive adjacent the end sections 48, the adhesive then engages between the front surface of the end sections and the front surface of the diaper adjacent the end sections. Alternatively, heat sealing means 90 may be located adjacent the rod 88 to secure the end sections 48 to the underlying front surface of the diapers. In either event, at this stage the fingers 80 are removed from the diapers by the spaced away downstream portions of the belts 82a and b to permit continued movement of the diapers.

The diapers 26 then pass under an endless belt 92 supported and driven by rollers 94 above the belts 74. The belt 92 is spaced slightly from the belts 74 in order to compress the end sections 48 of the diapers. The belts 92 and 74 thus form the folded over end sections 48 along fold lines 50, and provide a set to the adhesive if the depositing means 78 has been utilized to secure the end sections 48. The diapers then pass from the belts 74 and 92 into an apparatus 96 which may further fold the diapers along lateral central fold lines and package the folded diapers for use.

Thus, the device 70 first folds a flat diaper into a box-pleat configuration. Next, the device folds an end section of the box-pleat diaper including a portion of the backing sheet over the top of the diaper with a front surface of the end section facing the front surface of the diaper adjacent the end section. In addition, the device secures at least a portion of the front surface of the end section to the front surface of the diaper adjacent the end section. The end section may be secured in place either by adhesive deposited by the means 78 or by heat sealing the end section through use of the heat sealing means 90.

The foregoing detailed description is given for clearness of understanding only, and no unnecessary limitations should be understood therefrom, as modifications will be obvious to those skilled in the art.

I claim:

1. A disposable diaper, comprising: an absorbent pad, a liquid impervious backing sheet defining a back surface of the diaper, a front surface, a pair of side edges, a pair of end edges connecting the side edges, with said backing sheet extending to at least one end edge of the diaper, an end flap of the backing sheet adjacent said one end edge, said end flap being folded over the diaper with the front surface of the end flap facing the front surface of the diaper adjacent the end flap, and means for securing laterally spaced portions of said end flap to the front surface of the diaper to permit portions of the flap intermediate the securing means to gap away from the front surface of the diaper.

2. The diaper of claim 1 wherein said diaper has a plurality of longitudinal folds extending through said end edges and end flap and defining a box-pleat configuration of the diaper.

* * * * *